US00PP34483P2

(12) United States Plant Patent
Ren et al.

(10) Patent No.: US PP34,483 P2
(45) Date of Patent: Aug. 9, 2022

(54) WHITE WINE GRAPEVINE PLANT NAMED 'BLANC DU SOLEIL'

(50) Latin Name: ***Vitis* spp.**
Varietal Denomination: 'Blanc du Soleil'

(71) Applicant: Florida A&M University, Talahassee, FL (US)

(72) Inventors: Zhongbo Ren, Tallahassee, FL (US); Violeta Tsolova, Tallahassee, FL (US); Islam El-Sharkawy, Tallahassee, FL (US); Allen Frank Humphries, Tallahassee, FL (US); Jiang Lu, Shanghai (CN)

(73) Assignee: Florida A&M University, Tallahassee, FL (US)

( * ) Notice: Subject to any disclaimer, the term of this patent is extended or adjusted under 35 U.S.C. 154(b) by 0 days.

(21) Appl. No.: 17/300,669

(22) Filed: Sep. 20, 2021

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./207, 205
CPC ..... A01H 5/08; A01H 5/0812; A01H 5/00; A01H 6/688; A01H 6/08; A01H 6/88
See application file for complete search history.

(56) References Cited

U.S. PATENT DOCUMENTS

PP32,949 P2 * 4/2021 Walker ..... A01H 5/08 Plt./205
PP33,015 P2 * 5/2021 Walker ..... Plt./205

OTHER PUBLICATIONS

Goliad Advance Guard Harvest time 2020, retrieved on Oct. 20, 2021, retrieved from the Internet at https://www.mysoutex.com/goliad_advance_guard/news/features/harvest-time/article_38d64a5c-c51b-11ea-b4d8-fb32a567f28c.html, 2 pp. (Year: 2020).*

* cited by examiner

*Primary Examiner* — June Hwu
(74) *Attorney, Agent, or Firm* — Michele L. Lawson; Smith & Hopen, P.A.

(57) ABSTRACT

A new and distinct cultivars of grapevine, *Vitis* spp., which is an early to midseason ripening white wine grapevine that is resistant to Pierce's disease, exhibits low fruit ripening rot, and is able to produce premium white wines. The new and distinct cultivar produces a premium white wine with a pale yellow color and consistent yield. The cultivar has moderate-vigorous vine growth with moderate fruit yield. The cultivar produces wines with pale yellow color, smooth mouthfeel, and a harmonious blend of tropical fruit taste with a long and generous clear finish. The cultivar has inflorescences that develop generally from the $4^{th}$ to $6^{th}$ nodes of a shoot.

3 Drawing Sheets

Genus and species of new cultivar: *Vitis* spp.

BACKGROUND OF THE INVENTION

Florida and the southern grape industry are challenged by the prevalence of Pierce's disease (PD). The production of bunch grapes in the area has solely been based on a few hybrid grapes that could adapt to Florida's hot and humid climate and are tolerant or resistant to PD. Such grapes include 'Blanc du Bois', (Mortensen, J A., 1987—not patented); 'Suwannee', (Mortensen, J A., 1983—not patented); 'Stover', (Mortensen, J A., 1968—not patented); and 'Conquistador' (Mortensen, J A., 1983—not patented).

'Stover' (non-patented) is a self-fertile white grapevine released by J Mortensen in 1968. The cultivar was primarily developed as a dessert or table grape and was later found to be a fine wine grapevine. 'Stover' is resistant to PD, grows well in Florida, produces satisfactory yields, and maintains easy and simple canopy management due to its moderate vigor. Its small loose cluster is an additional advantage of lowering the fruit rot during ripening.

'Blanc du Bois' (non-patented) was released by J Mortensen in 1987 as a white wine grapevine. It is self-fertile, PD resistant, and able to produce premium wine with a rich muscat aroma. This cultivar made spicy white wine rated as premium quality. The delicate sugar/acid balance plus the presence of muscatel flavor in the juice have given 'Blanc du Bois' a prominent place among Florida's wines.

Despite the distinguishing characteristics of these cultivars, continuous improvement for better wine cultivars has been required by the Florida grape industry due to the development of market diversity and the problems with current cultivars. For example, the production of these grapes is costly due to their susceptibility to other hot-humid-related diseases such as anthracnose, which requires heavy spray programs. The ripe rot of 'Blanc du Bois' during ripening has been a severe problem for both growers and wineries. Further, special vineyard management, grafting for example, is required for the weakness of 'Stover'. Therefore, the Florida grape industry has been demanding new cultivar with improved horticulture traits and better premium wine profiles, better integration of disease resistance, good commercial productivity, distinguished rich flavor and stable color of wines.

BRIEF SUMMARY OF THE INVENTION

'Blanc du Soleil' (*Vitis* spp.) is the new early to midseason ripening white wine grape cultivars bred for the grape industries in Florida, Texas, and the Southeastern United States (hardiness zone of 8, 9, and 10). The cultivar exhibits good Pierce Disease (PD's) tolerance and can produce a high-quality wine with varietal character and satisfactory yield.

The following traits have been repeatedly observed when vine is grown under its own roots and are the most pronounced characteristics of this new cultivar when grown in Florida and Texas, and which in combination distinguish it from existing cultivars:

1) PD-resistant grapevine.
2) Satisfactory yield with a lower rot fruit rate during ripening.
3) Majority fruit clusters grow at the $4^{th}$ to $6^{th}$ node.
4) Both the asexual propagation and enology procedures of the new cultivars showed that its distinguishing traits come truly established and transmitted through succeeding propagation.

BRIEF DESCRIPTION OF THE DRAWINGS

The accompanying color photographs show a representative section of a typical specimen of the new cultivar.

DETAILED BOTANICAL DESCRIPTION

Figure 1:
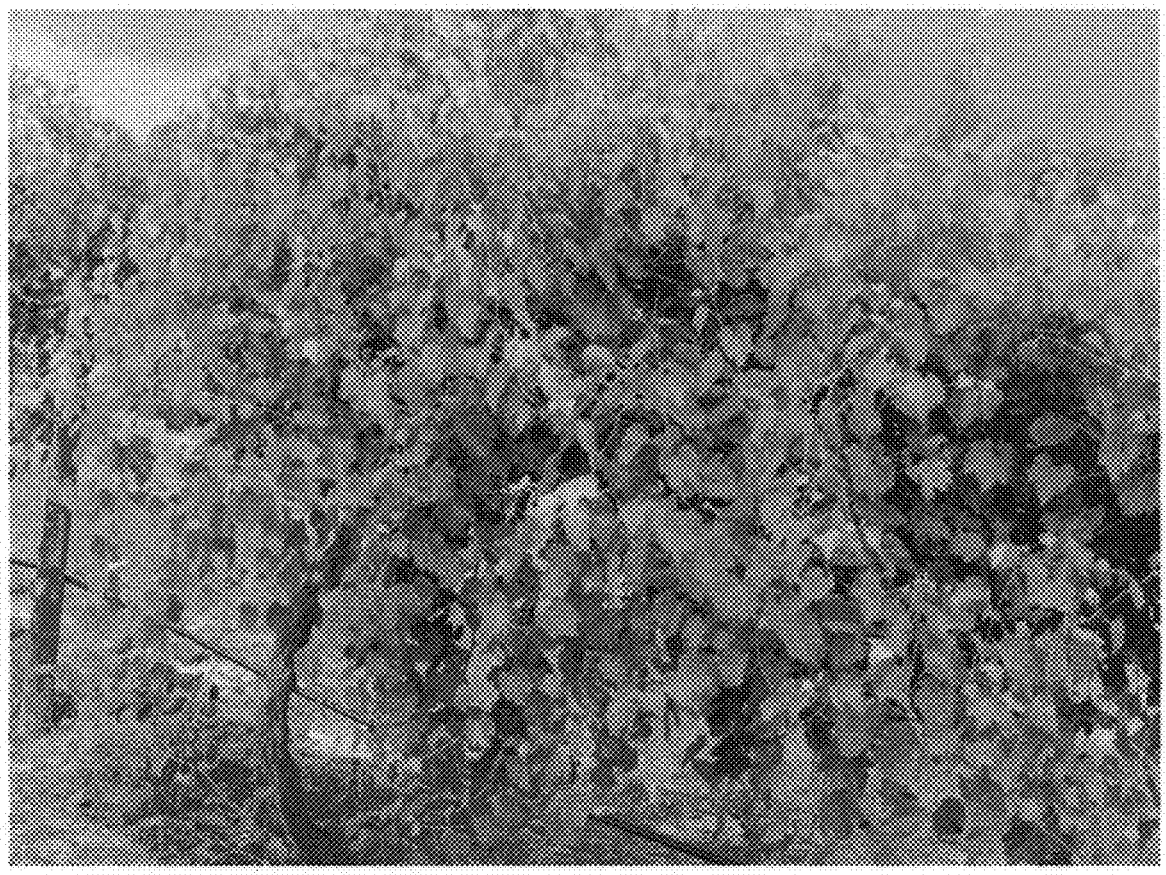
FIG. 1 is a perspective view of a 11-year-old 'Blanc du Soleil' vine and canopy with semi-erect growth habit under doble cordon training and spur pruning at midseason.

In the following description, color references are made as per *The Royal Horticultural Society Colour Chart* (R.H.S.), The Royal Horticultural Society, London, 2015 (sixth edition) except where general terms of ordinary dictionary significance are used.

Origin of the Cultivar

'Blanc du Soleil' originated from a seedlings' population crossed between Florida's non-patented cultivars 'Stover' (*Vitis* spp.) and 'Blanc du Bois' (*Vitis* spp.) in 1999. The seedling was selected from a progeny of 137 and was planted in Tallahassee, Fla. in the spring of 2001.The seedling was noticed first for its high disease resistance as well as its early and better fruiting traits in 2005. The comparative evaluation for the agronomic and enological characteristics of the selection was initiated in 2016 in Tallahassee, Fla. and in College Station, Tex. on vines grown on its own roots.

The new cultivar 'Blanc du Soleil' results from directed cross-hybridization of 'Stover' X 'Blanc du Bois', cvs. and possesses unique genotypic and phenotypic characteristics. The specific and original features of the new cultivar have been retained via vegetative propagation by layering, dormant and soft cuttings. 'Blanc du Soleil' demonstrates higher tolerance to freeze damage under late spring frost conditions and higher anthracnose and fruit rot resistance than its parent 'Blanc du Bois'. As an advantage to 'Stover' the new cultivar doesn't require grafting and can be grown on its own roots in Florida and southeastern U.S.

Methods of Asexual Reproduction

'Blanc du Soleil' was asexually reproduced by layering, dormant and soft cuttings in the research vineyards of the Center for Viticulture and Small Fruit Research, Florida A&M University (FAMU), 6361 Mahan Drive, Tallahassee, Fla. 32308. 'Blanc du Soleil' originated from a cross of the non-patented *Vitis* spp. cultivars 'Stover'-female parent (*Vitis* spp.) and 'Blanc du Bois' male-pollinator (*Vitis* spp.) in 1999. The new cultivar has been evaluated under the experimental designation "A24-5-6". The unique features of the new cultivar have been retained.

Plant Characteristics

The following phenotypical characteristics are relevant for vines that are 11 years old.

Vine

The vines of 'Blanc du Soleil' grow moderately, i.e., the growth of a shoot on mature vines is about 3 to 6 feet per growing season. The vines generally fill 10 feet single-wire trellis in the second growing season in Florida. The pruning weight is 3.4 lb/vine from the 10-feet canopy vines with a 2-arm cordon single wire training system and spur pruning technics, which is lower than that of 'Blanc du Bois', while is higher than that of 'Stover' (Table 1).

The trunk is strong and well developed with the average trunk diameter of an 11-years-old vine being 7.7 cm. The trunk surface is roughly textured with a fibrous, shaggy exterior skin. The color of the trunk wood surface is greyish reddish-orange (RHS 177D).

Canes

Canes are strong with 2-years old cane averaging 1.8 cm in diameter, with light brownish grey (RHS 201B) and moderate shatter.

The dormant buds are 5.1×4.6 mm (W×L), with medium brown coloration (RHS 200C).

Shoots

The young 'Blanc du Soleil' shoots are semi-closed with greyed red (RHS 176A) color during blooming. Both upper and underneath color of the young leaf is greyed red (RHS 176A).

Young shoot tip is with medium prostrate hairs with weak anthocyanin color of moderate reddish orange (RHS179C).

There are no visual prostrate hairs between the veins on the lower young leaf surface, but there are medium erect heirs present on the main veins.

Tendrils averaged 13 cm with sparse to medium mixed prostrate and erect hairs. Tendril tip is greyed red (RHS 176A) in color and more color deposit at the tendril tips than the other parts of a tendril.

Mature woody shoots grow semi-erect (FIG. 1) with old shoot cross-section being smooth. The woody shoot is with smooth surface and internode's dorsal side color of moderate reddish brown (RHS 177A) and ventral side of internode-greyish brown (RHS 166A).

The dorsal side of the node is the dark greyish reddish brown (RHS 200A) and ventral side color of moderate brown (RHS 200C).

Foliage

'Blanc du Soleil' bear mid-sized leaves with mature leaf blade averaging 7.3×9.4 cm (L×W). Color of mature leaves are moderate olive green (RHS 137B) on the abaxial side blade and moderate yellow-green (RHS 147B) on the adaxial side blade. Mature leaf teeth length is medium Anthocyanin coloration of the main veins on the upper surface of the mature leaf is absent.

'Blanc du Soleil' bear pentagonal-shaped leaves with five (5) lobes. The leaf teeth are a mixture of one side concave, one side convex, and both sides straight—leaf profile from flat to very shallow V-shape. There are smooth surfaces of both the abaxial and adaxial sides of the leaves. The venation pattern of the leaves is netted or reticulate with light-yellow-green coloration (RHS142D).

Petiole length is shorter than middle vein length. Petiole color is light reddish brown (RHS 177B). The petiole sinus is wide open, and the depth of the upper lateral sinuses is shallow.

Inflorescences

Inflorescences generally developed from the $4^{th}$ to $6^{th}$ nodes of a shoot. Both male and female organs of flowers are fully developed, and they are hermaphrodite (self-fertile, perfect) flowers with the diameter (D) 1.5 mm and height (H) 3.0 mm.

The color of un-open flower at blooming time is moderate yellow-green (RHS 146C). The ovary of an opening flower is strong greenish-yellow (RHS 153B). The anthers are strong yellow (RHS 153D) in color.

Fruit Cluster (Bunch)

The mature bunch is medium size with an average weight (WG) of 108.6 g, length (L) of 15.7 cm, and width (W) of 12.1 cm.

The primary peduncle of the bunch is short with average length of 1.2 cm, no lignification, and weak anthocyanin coloration.

Figure 2:
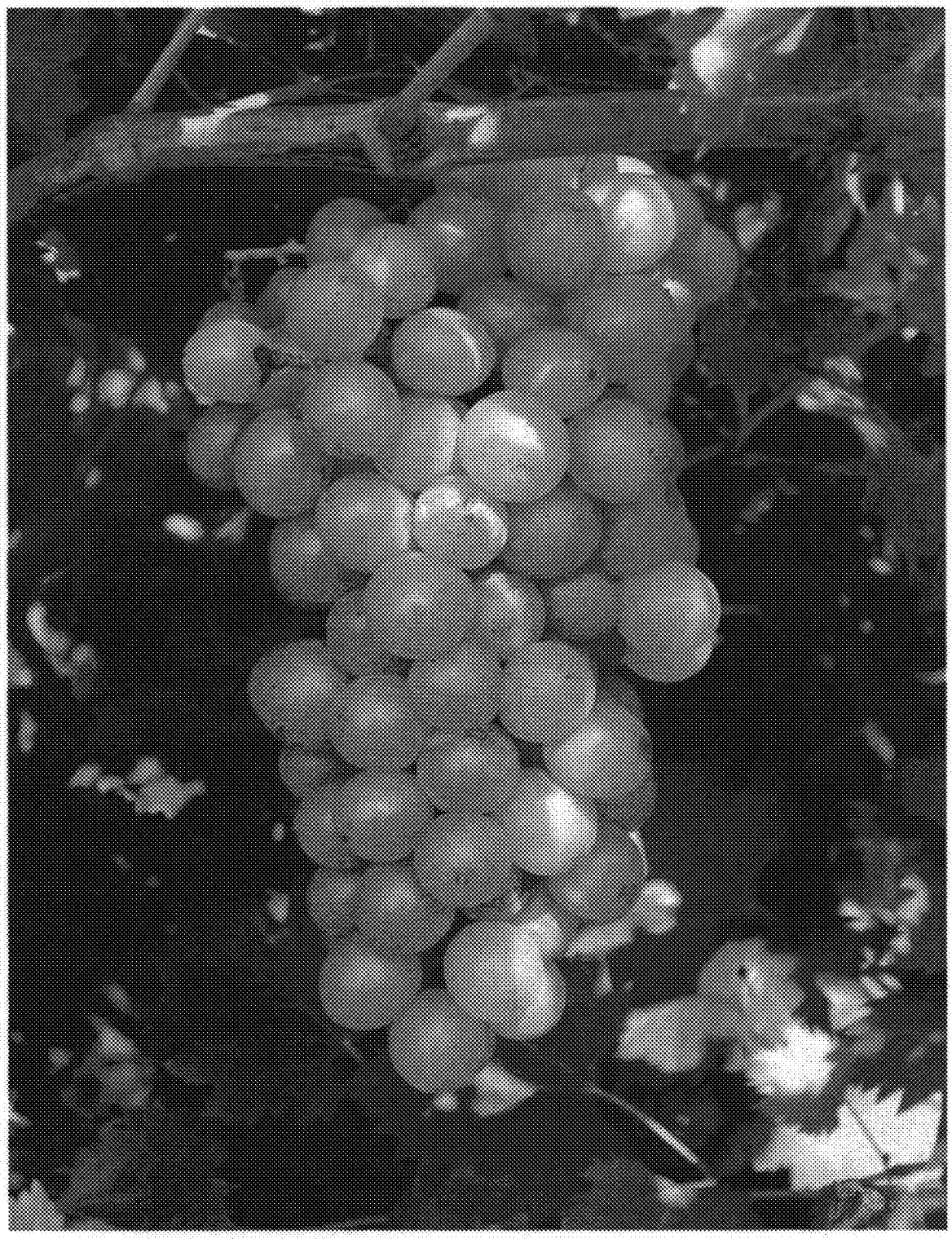
FIG. 2 is a perspective view of a fruit cluster on the vine in fruit maturity of a 11-year-old vine.

Mid-sized fruit clusters are semi-dense, each bearing 33 fruits (berries) on average. (FIG. 2). Pedicels are not visible to slightly visible. Fruits are generally partially movable however it is difficult to detach fruits from pedicels.

Figure 3:
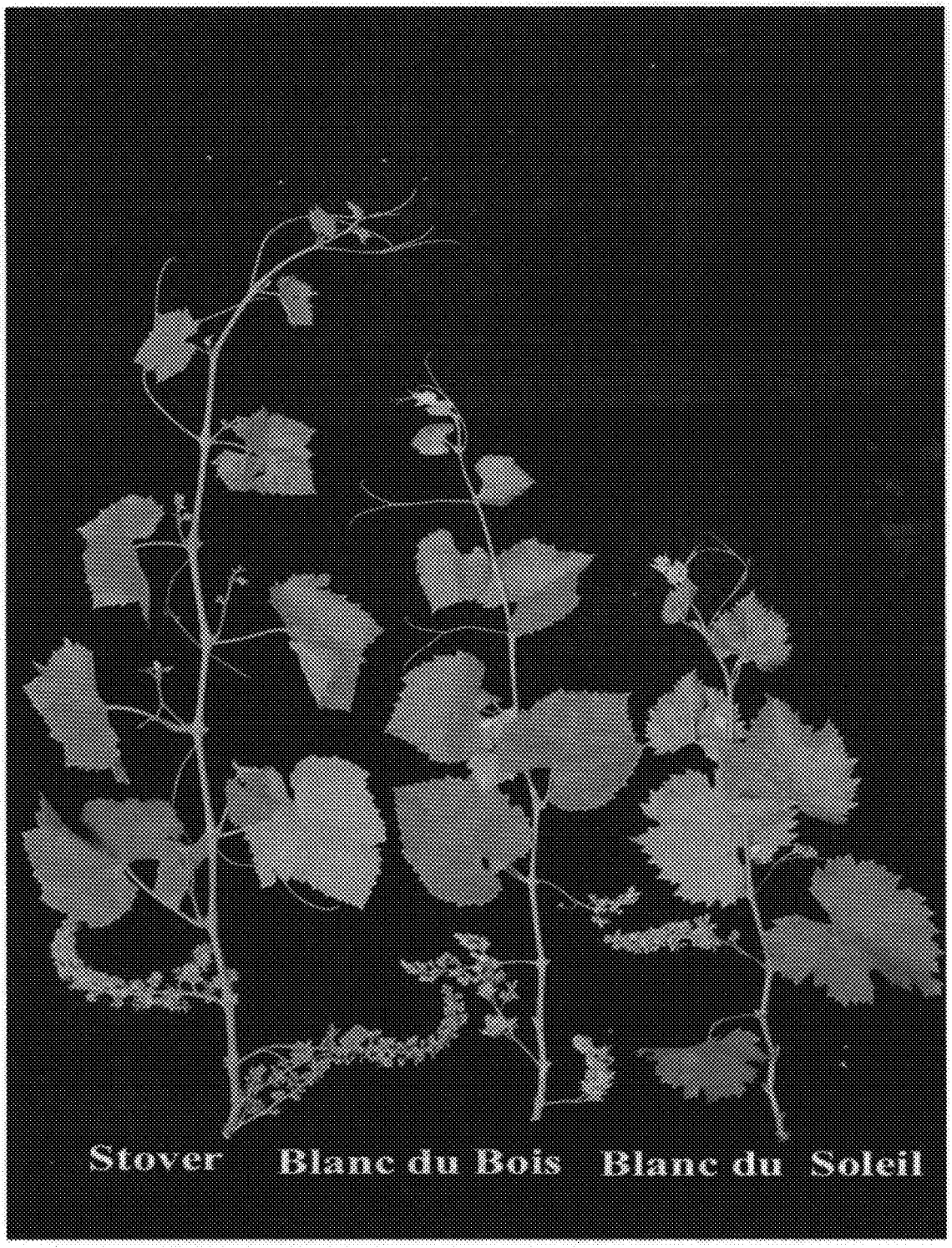
FIG. 3 is a perspective view of a typical young fruiting shoot of 'Blanc du Soleil' showing two clusters developed at the $4^{th}$ and $5^{th}$ nodes in comparison with typical fruiting shoots of 'Stover' and 'Blanc du Bois' cvs.

Fruit clusters develop mostly at the 4th to 6th nodes from the base of the young shoot (FIG. 3). Accordingly, 'Blanc du Soleil' is better suited to cane pruning or long-spur pruning techniques, as its canes are most fruitful at a considerable distance from the base, mostly at the $4^{th}$ to $6^{th}$ nodes.

Fruits

The berry of 'Blanc du Soleil' is slightly oblong to round shape, 1.7 cm×1.6 cm (L×D) in size and 2.5 g in weight. Fruit skin is medium-thin and smooth, with strong greenish, yellow (RHS 153C) color (without bloom). The fruit flesh is semi-soft with pale greenish-yellow (RHS 160C) color at peak ripening and absent anthocyanin coloration.

The seeds of 'Blanc du Soleil' are large and high weight with the average weight being 53.3 mg, which is larger than the seeds of 'Stover' and 'Blanc du Bois' (Table 2). The berry seed is with average length (L) of 6.1 mm and greyish reddish brown color (RHS 200B).

The flavor of fresh fruits is fruity—neutral and very pleasant. 'Blanc du Soleil' fruit juice contains 17.6% sugar level, 0.64 g/L titratable acid, and pH 2.96 (Table 2), which are the desirable traits in producing premium wines.

Productivity

'Blanc du Soleil' produces a moderate yield capacity and a spur fertility rate of 90%. An average of 12 lbs. of fruit is harvested from 10-feet canopy vines with 2-arm cordon single wire training system and spur pruning technics. The yield is lower than that of 'Blanc du Bois' and is similar to the yield of 'Stover' (Table 2). Similarly, a spur of 'Blanc du Soleil' produced 223 g fruit, which is the same as that of 'Stover', but obviously lower than the 428 g spur productivity of 'Blanc du Bois' (Table 2).

The productivity of 'Blanc du Soleil' may be further improved by applying long spur (5 to 6 bud spur) or cane pruning technics.

Annual Growth Cycle of the Grapevine

'Blanc du Soleil' buds break in early March, flowering occurs from mid-April to later April, with fruits setting in early May, fruits ripening in mid to later July, and leaves falling in December in Tallahassee, Fla.

Disease/Pest Resistance or Susceptibility

Neither PD nor anthracnose symptoms have been observed during the 11-year evaluation in Tallahassee, Fla. The ripening fruit rot rate of 'Blanc du Soleil' is lower than that of 'Blanc du Bois' (Table 1).

TABLE 1

Horticultural characteristics of 'Blanc du Soleil' and premium Florida wine cultivars (3-year average data)

| | vine vigor | pruning weight (ib/vine) | internode (L × D, cm) | leaf size L × W, cm) |
|---|---|---|---|---|
| 'Blanc du Bois' | vigor | 5.2 | 8.0 × 1.05 | 9.1 × 12.2 |
| 'Stover' | w.~moderate | 2.6 | 5.4 × 0.82 | 6.8 × 8.5 |
| 'Blanc du Soleil' | moderate | 3.4 | 5.8 × 0.91 | 7.3 × 9.3 |

| | fruiting node | PD symptoms (0~5) | anthracnose (0~5) | fruit rot rate (%) |
|---|---|---|---|---|
| 'Blanc du Bois' | 2~4 | occasional | 3 | 37 |
| 'Stover' | 2~4 | occasional | 2 | 4 |
| 'Blanc du Soleil' | 4~6 | 0 | 0 | 4 |

TABLE 2

Productivity, fruit and juice characteristics of 'Blanc du Soleil' and premium Florida wine cultivars (3-year average data)

| | spur fertility (%) | fruit cluster/ spur | fruit number/ cluster | spur fruit weight (g) | yield (Ib/vine) | fruit size (g) |
|---|---|---|---|---|---|---|
| 'Blanc du Bois' | 94 | 3.6 | 42 | 428 | 19 | 2.8 |
| 'Stover' | 98 | 4.5 | 21 | 277 | 13 | 2.4 |
| 'Blanc du Soleil' | 90 | 2.7 | 33 | 223 | 12 | 2.5 |

| | seed size (mg) | SSC (%) | pH | TA (g/L) | wine color intensity[y] | wine color Hue[x] |
|---|---|---|---|---|---|---|
| 'Blanc du Bois' | 33 | 17.9 | 3.05 | 0.57 | 0.213 | 3.05 |
| 'Stover' | 44 | 15.2 | 3.08 | 0.51 | — | — |
| 'Blanc du Soleil' | 53 | 17.6 | 2.96 | 0.64 | 0.143 | 2.97 |

[y]absorbance of 420 nm/520 nm

[x]absorbance of 420 nm + 520 nm

TABLE 3

Vinification parameters for 'Blanc du Soleil' and premium Florida wine cultivars (experimental wine vintages 2018, 2019, and 2020) (3-year average data)

| Variety | Density (g/mL) | Alc % per Vol | Net Dry Matter (g/L) | pH | Titratable Acidity (g/L TAE) | Volatile acidity (g/L AAE) |
|---|---|---|---|---|---|---|
| 'Blanc du Soleil' | 0.9908 | 12.2 | 24.1 | 3.1 | 8.1 | 0.4 |
| 'Blanc du Bois' | 0.9905 | 12.6 | 20.2 | 3.2 | 9.4 | 0.4 |
| 'Stover' | 0.9891 | 13.4 | 18.9 | 2.8 | 7.5 | 0.3 |

| Variety | OD 420 | OD 520 | OD 620 | Intensity | Hue |
|---|---|---|---|---|---|
| 'Blanc du Soleil' | 0.107 | 0.034 | 0.012 | 0.153 | 3.168 |
| 'Blanc du Bois' | 0.143 | 0.043 | 0.016 | 0.202 | 3.627 |
| 'Stover' | 0.079 | 0.032 | 0.008 | 0.119 | 2.385 |

TAE: Tartaric acid equivalent
AAE: Acetic acid equivalent
OD: Optical density
Intensity: OD 420 + OD 520 + OD 620, Hue: OD 420/OD 520

What is claimed is:

1. A new and distinct cultivars of grapevine named 'Blanc du Soleil', substantially as herein described and illustrated.

* * * * *